US008343554B2

(12) United States Patent
Bombardelli

(10) Patent No.: US 8,343,554 B2
(45) Date of Patent: Jan. 1, 2013

(54) FORMULATIONS FOR THE TREATMENT OF ARTHRITIS CONDITIONS

(75) Inventor: Ezio Bombardelli, Gropello Cairoli (IT)

(73) Assignee: Indena S.p.A., Milan (IT)

( * ) Notice: Subject to any disclaimer, the term of this patent is extended or adjusted under 35 U.S.C. 154(b) by 655 days.

(21) Appl. No.: 10/562,205

(22) PCT Filed: Jan. 6, 2004

(86) PCT No.: PCT/EP2004/005875
§ 371 (c)(1),
(2), (4) Date: May 15, 2006

(87) PCT Pub. No.: WO2005/002611
PCT Pub. Date: Jan. 13, 2005

(65) Prior Publication Data
US 2006/0280811 A1   Dec. 14, 2006

(30) Foreign Application Priority Data

Jun. 27, 2003   (IT) .............................. MI2003A1311

(51) Int. Cl.
*A61K 36/82* (2006.01)
*A61K 36/00* (2006.01)
*A61K 31/70* (2006.01)
(52) U.S. Cl. ........................... 424/729; 424/769; 514/62
(58) Field of Classification Search ........................ None
See application file for complete search history.

(56) References Cited

U.S. PATENT DOCUMENTS

| | | | |
|---|---|---|---|
| 3,679,707 A * | 7/1972 | Yoshimura et al. ........... | 549/335 |
| 4,710,491 A * | 12/1987 | Lockhoff et al. ............... | 514/42 |
| 4,870,061 A | 9/1989 | Speck | |
| 5,629,351 A | 5/1997 | Taneja et al. | |
| 5,762,936 A * | 6/1998 | Ronzio et al. ................. | 424/757 |
| 6,107,334 A * | 8/2000 | Chilton ......................... | 514/464 |
| 6,541,045 B1 * | 4/2003 | Charters et al. ............... | 424/737 |
| 2002/0010168 A1 | 1/2002 | Ammon et al. | |
| 2002/0032171 A1 * | 3/2002 | Chen et al. ..................... | 514/54 |

FOREIGN PATENT DOCUMENTS

| | | |
|---|---|---|
| EP | 0 864 580 | 9/1989 |
| GB | 1 015 800 | 1/1966 |

OTHER PUBLICATIONS

Belch et al., Evening Primrose oil and borage oil in rheumatologic conditions, 2000, 71: 352s-356s.*
http://www.mcp.edu/herbal/default.htm.*
http://www.medicineword.com/glucurone.shtml.*
USDA http://plants.usda.gov/java/profile?symbol=OEBI.*
Nonaka et al., Tannins and related compunds 15. A new class of dimeric flavan-3-ol gallates theasinensin A and Theasinensen B and Proanthocyanidin glaates from green tea theasinensis leaf, 1983, Chemical and Pharmaceutical Bulletin, 31, 3906-3914.*
PracticalTherapeutics Foster, Reference-Book of Practical Therapeutics, 1897, vol. II, D. Appleton and Co., New York, p. 147.*
Sato et al., A phtoelectric method for estimating inflammatory intensity in mice and its application to the anti-inflammatory evaluation to the anti-inflammatory evaluation of glucuronic acid derivatives, 1967, Jap. J. Pharmacol., 17, 557-571.*
Chrubasik S et al: "Treatment of Rheumatic Pain With Herbal Medicine in Europe" Pain Digest, Springer, New York, NY, US, vol. 8, No. 4, 1998, pp. 231-236, XP009O14438, ISSN; 0938-9016,p. 231, col. 1, paragraphs 2,3 table 2.
Database Medline 'Online! US National Library of Medicine (NLM), Bethesda, MD, US; 2002, Chrubasii( Sigrun et al: "'Pain management with herbal antirheumatic drugs!" XPOO2298411, Database accession No. NLM12O17748 abstract, abstract & Wiener Medizinische Wochensonrifi (1946) 2002, vol. 152, No. 7-s, 2002, pp. 198-203, 155W; 0043-5341.
Database Medline 'Online! US National Library of Medicine (NLM), Bethesda, MD, US;Sep. 1999, Zhao J et al: Anti-tumor-promoting activity of a polyphenolic fraction Isolated from grape seeds in the mouse skin two-stage Initiation-promotion protocol and identification of procyanidin B5-3'-gallate as the most effective antioxidant constituent, XPO02298412, Database accession No. NLM10469619, abstract: 1st sentence, abstract & CARCINO3ENESIS. Sep. 1999, vol. 20, No. 9, Sep. 1999, pp. 1737-1745, 155W: 0143-3334.
Tamai Y et al: "Enhanced healing of cartilaginous injuries by N-acetyl-d-glucosamine and glucuronic acid"Carbohydrate Polymers, Applied Science Publishers, Ltd. Barking, GB, vol. 54, No. 2, Nov. 1, 2003, pp. 251-262, XP004452621, 155W: 0144-8617, abstract,.p. 262, col. 1, paragraph 2.

* cited by examiner

*Primary Examiner* — Michele C. Flood
*Assistant Examiner* — Catheryne Chen
(74) *Attorney, Agent, or Firm* — Young & Thompson

(57) ABSTRACT

The present invention relates to formulations comprising combinations of analgesic/anti-inflammatory, immunomodulating and cartilage-reconstructing agents in particular comprising saligenig, boswellic acid, procyanidins, N-acetyglucosamine and either glucuronic acid or glucoronolactone, for the treatment of rheumatoid arthritis and, more generally, of arthritis conditions.

2 Claims, No Drawings

FORMULATIONS FOR THE TREATMENT OF ARTHRITIS CONDITIONS

FIELD OF THE INVENTION

The present invention relates to formulations comprising combinations of analgesic/anti-inflammatory, immuno-modulating and cartilage-reconstructing agents for the treatment of rheumatoid arthritis and, more generally, of arthritis conditions.

The combination of these agents, acting through different mechanisms of actions, reduces pain and prevents the progression of articulation injuries.

TECHNOLOGICAL BACKGROUND

Rheumatoid arthritis is a chronic degenerative disease which affects a large portion of the elderly, causing serious problems to patients. The pathogenesis of rheumatoid arthritis and arthritis conditions is due at first to the immune system, and subsequently to inflammatory conditions which erode the intra-articular surfaces causing deforming damages which are irreversible and painful.

DISCLOSURE OF THE INVENTION

The present invention relates to compositions comprising a combination of active principles capable of inducing particularly effective therapeutic effects, without important side effects even after prolonged treatments.

The pharmaceutical formulations of the invention comprise:
- pure saligenin or derivatives thereof or extracts containing them selected from saligenin-enriched *Salix rubra* extract;
- substantially pure boswellic acid or a semi-synthetic derivative thereof or a boswellic acid-enriched *Boswellia serrata* extract;
- procyanindins from *Vitis vinifera* or from *Camellia sinensis* or rhein or lipophilic derivatives thereof;
- N-acetyl-glucosamine;
- glucuronic acid or glucuronolactone.

Examples of saligenin derivatives comprise the acetic or butyric esters, whereas examples of boswellic acid derivatives comprise pharmaceutically acceptable salts or esters.

The formulations of the invention preferably comprise:
*Salix rubra* extract containing 25% by weight of saligenin;
*Boswellia serrata* extract containing 20% by weight of boswellic acid;
procyanindins from *Vitis vinifera* or from *Camellia sinensis* optionally complexed with phospholipids or rhein or lipophilic derivatives thereof;
N-acetyl-glucosamine;
glucuronic acid or glucuronolactone.

The *Salix rubra* extract, the *Boswellia serrata* extract, procyanindins, N-acetyl-glucosamine, glucuronic acid or glucuronolactone are preferably present in the formulations in 2:1:1:1:1 weight ratios, respectively.

The formulations will contain typically 100 to 500 mg of 25% *Salix* extract, 50 to 150 mg of procyanindins optionally in the form of complexes with phospholipids, 20 to 200 mg of *Boswellia serrata* extract, 10 to 500 mg each of glucosamine and glucuronic acid or glucuronolactone.

The proanthocyanidins from *Vitis vinifera* can be obtained according to what disclosed in GB-A-1541469 or FR-A-2092743 or in EP 348781, while the corresponding phospholipid complexes are known from U.S. Pat. No. 4,963,527; *Camellia sinensis* extracts are disclosed, for example, in EP 814823.

*Boswellia* and boswellic acid extracts can be prepared according to known methods, and are commercially available as well the saligenin-enriched *Salix rubra* extracts.

The formulations will be in the form of soft- or hard-gelatin capsules, tablets or other forms suitable for the oral administration. Preferred are the capsules containing *Enothera biennis* oil as the carrier.

The procyanindins from *Vitis vinifera* or *Camellia sinensis* exert anti-radicalic action and inhibit proteoglycans-hydrolysing metal-proteases; they also synergistically interact with the cyclooxygenase 2 (COX-2) inhibiting components present in the *Salix* and *Boswellia* extracts.

As an alternative to proanthocyanidins, certain anthraquinones, mainly rhein or lipophilic derivatives thereof such as diacerhein, may be used, which reduce cell proliferation and stimulate proteoglycan synthesis.

N-Acetyl-glucosamine, glucuronic acid or glucuronolactone, which can be considered the building blocks of the connective tissue, complete the therapeutic profile of the formulations of the invention, as they promote the resynthesis of proteoglycans in the joints, which is an important restoration process that, together with the aforementioned factors, can contribute to a symptomatic improvement.

The compositions of the invention can be administered for prolonged times, in one or repeated daily administrations, until recovery or relief from the symptoms.

The following examples further illustrate the invention.

EXAMPLE I

Preparation of Cellulose Capsules

Each capsule contains:

| | |
|---|---|
| *Salix rubra* extract (25% in saligenin) | 200 mg |
| *Boswellia serrata* extract (20% in boswellic acid) | 100 mg |
| Green Tea extract (70% in procyanidins) | 100 mg |
| N-Acetyl-glucosamine | 100 mg |
| Glucuronolactone | 100 mg |
| *Enothera biennis* oil | q.s. to 700 mg |

EXAMPLE II

Preparation of Capsules

Each capsule contains:

| | |
|---|---|
| *Salix* extract (25% in saligenin) | 200 mg |
| *Boswellia serrata* extract (20% in boswellic acid) | 100 mg |
| Diacerhein | 100 mg |
| N-acetyl-Glucosamine | 100 mg |
| Glucuronolactone | 100 mg |
| *Enothera biennis* oil | q.s. to 700 mg |

The formulation of the Example I, when administered to patients suffering from rheumatoid arthritis or arthritis conditions, showed consistent clinical results in terms of pain reduction, better mobility of the affected limbs, biopsic examinations of the joints and sense of well-being.

The invention claimed is:

1. A formulation comprising *Salix rubra* extract containing 25% by weight of saligenin, *Boswellia serrata* extract containing 20% by weight of boswellic acid, *Camellia sinensis* extract containing 70% by weight of procyanidins, N-acetyl-glucosamine and glucuronolactone, wherein the *Salix rubra* extract, the *Boswellia serrata* extract, the *Camellia sinensis* extract, N-acetyl-glucosamine, and glucuronolactone are present in a 2:1:1:1:1 weight ratios, respectively.

2. The formulation as claimed in claim 1 in the form of capsules containing *Enothera biennis* oil as a carrier.

* * * * *

UNITED STATES PATENT AND TRADEMARK OFFICE
CERTIFICATE OF CORRECTION

| | | |
|---|---|---|
| PATENT NO. | : 8,343,554 B2 | Page 1 of 1 |
| APPLICATION NO. | : 10/562205 | |
| DATED | : January 1, 2013 | |
| INVENTOR(S) | : Ezio Bombardelli | |

It is certified that error appears in the above-identified patent and that said Letters Patent is hereby corrected as shown below:

On the title page, please amend Item (22) to read as follows:

-- (22) PCT Filed: June 1, 2004 --

Signed and Sealed this
Nineteenth Day of February, 2013

Teresa Stanek Rea
*Acting Director of the United States Patent and Trademark Office*